(12) United States Patent
Nissilä

(10) Patent No.: US 7,177,672 B2
(45) Date of Patent: Feb. 13, 2007

(54) CODING HEART RATE INFORMATION

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 10/735,255

(22) Filed: Dec. 12, 2003

(65) Prior Publication Data

US 2004/0143193 A1    Jul. 22, 2004

(30) Foreign Application Priority Data

Dec. 16, 2002    (FI) ................................ 20022200

(51) Int. Cl.
*A61B 5/04* (2006.01)

(52) U.S. Cl. .............. 600/519; 600/500; 600/508; 600/514

(58) Field of Classification Search ........... 600/500, 600/508, 514, 519
See application file for complete search history.

(56) References Cited

U.S. PATENT DOCUMENTS

| | | | |
|---|---|---|---|
| 5,267,942 A * | 12/1993 | Saperston | 600/28 |
| 5,621,805 A | 4/1997 | Loh et al. | |
| 5,730,140 A | 3/1998 | Fitch | |
| 5,986,200 A * | 11/1999 | Curtin | 84/609 |
| 6,230,047 B1 * | 5/2001 | McHugh | 600/519 |
| 6,572,511 B1 * | 6/2003 | Volpe | 482/4 |
| 2002/0138013 A1 | 9/2002 | Guerrero et al. | |

FOREIGN PATENT DOCUMENTS

| | | |
|---|---|---|
| DE | 3546052 A1 | 6/1987 |
| FR | 2827069 | 1/2003 |
| JP | 08186495 | 7/1996 |
| WO | WO 01/37914 A1 | 5/2001 |
| WO | WO 03/005339 A1 * | 1/2003 |

OTHER PUBLICATIONS

Finnish Official Action issued in corresponding Finnish Application No. 20022200.

* cited by examiner

*Primary Examiner*—Robert L. Masser
*Assistant Examiner*—Patricia Mallari
(74) *Attorney, Agent, or Firm*—Hoffman & Baron, LLP

(57) ABSTRACT

The invention relates to an arrangement for coding heart rate information, comprising means (600A, 600B) for measuring a person's heart beat intervals and means for storing (648) the measured heart beat interval information. The arrangement comprises means (654) for coding the heart beat interval information stored in the storing means (648) into music, the coding means comprising means (660) for selecting the rhythm of the music on the basis of the measured heart beat intervals.

20 Claims, 4 Drawing Sheets

CODING HEART RATE INFORMATION

CROSS-REFERENCE TO RELATED APPLICATION

This application claims priority based on Finnish Patent Application No. 20022200, filed on Dec. 16, 2003.

FIELD OF THE INVENTION

The invention relates to processing heart beat interval information measured on a human.

BRIEF DESCRIPTION OF THE RELATED ART

In connection with a physical exercise it is possible to measure a person's heart rate information by means of a heart rate monitor, for instance. The information obtained during the exercise can be stored in a memory of the heart rate monitor and transferred after the exercise to a separate microcomputer, for instance, for further analysis. Conventionally, the analysis has covered observation of temporal variations in the heart rate in the coordinates.

The prior art manner to render abundant and complicated data into an easily manageable, observable and detectable form is not optimal.

SUMMARY OF THE INVENTION

It is an object of the invention to provide an improved method and equipment for converting the presentation mode of stored heart rate information to a format that can be easily processed. This is achieved with a method for coding heart rate information, which method measures a person's heart beat intervals during a physical exercise and stores the measured heart beat interval information. The method codes the measured and stored heart beat interval information into music after the physical exercise such that the rhythm of the music depends on the measured heart beat intervals.

The invention also relates to an arrangement for coding heart rate information comprising means for measuring a person's heart beat intervals and means for storing the measured heart beat interval information. The arrangement comprises means for coding the heart beat interval information stored in storing means into music, the coding means comprising means for selecting the rhythm of the music on the basis of the measured heart beat intervals.

Thus, it is an object of the invention to provide a method and equipment for coding heart rate information, which coding refers here to changing the presentation mode of the information. The heart rate information to be measured on a person during a physical exercise, i.e. the heart beat interval information refers to a measured heart rate level and variations therein at different time instants. The measuring can be performed during a physically or mentally strenuous performance, such as a physical exercise or contest.

The solution of the invention produces music, for which the tempo is selected on the basis of variations in the heart beat intervals. Hence, as the heart beat intervals become shorter and the heart rate rises the tempo accelerates.

In one embodiment, the producer of music, such as the user, selects a musical genre prior to production. The genre may be jazz, heavy rock, pop, classical music or the like.

Music can be produced digitally, for instance, whereby it is possible to utilize a digital music bank. In the music bank, music can be stored as sound packets classified according to different genres. Further, the sound packets can be classified according to different instruments such that the guitar, the drums and the saxophone are each sorted out into separate sound packet groups. Thus, the acceleration of the tempo according to the invention refers to shortening the sound packet intervals, whereby the beat of the music becomes faster.

In one embodiment the sound scale of music is augmented when the length of a heart beat interval is below a predetermined threshold value. Thus, as the heart beat interval becomes shorter and the heart rate rises, the sound scale of the produced music is expanded by adding the number of instruments, for instance. For instance, if at the heart rate of less than 100 beats/minute the music employs only one instrument, at the level exceeding 100 beats/minute the music can be generated by two sounds. Correspondingly, the sound world can be expanded when the measured heart beat interval information indicates that the duration of the exercise has exceeded the predetermined threshold value. Thus, for instance the sound scale can be expanded at the interval of every five minutes. The time threshold value used may also change with the heart rate level, for instance, such that at the heart rate level of 100 to 140 the sound scale is expanded at the interval of every five minutes but within the range of 140 to 160 the expansion takes place at the interval of every two minutes.

In one embodiment the rhythmical complexity of the music is increased as the variations in the heart beat intervals increase. This means that when the heart rate has an ascending or a descending trend, variation is added to the rhythm around the average rhythm determined by the heart beat interval. For instance, if the repetition interval of packets, i.e. the rhythm at a given heart rate level is 20 ms with standard deviation +/−1 ms, the standard deviation can be raised to 5 ms, for instance, by increasing the rhythmical complexity.

In one embodiment the volume of the produced music is raised when the heart beat interval becomes shorter than the predetermined threshold value. So, a rise in the heart rate can be indicated by raising the volume, and in a corresponding manner, the volume is reduced as the heart rate comes down.

The heart rate measuring takes place during a physically/mentally strenuous exercise. Thus, there are sufficiently variations in the heart rate and the music to be produced will be rich and diverse in its content and expression.

In one embodiment the heart beat interval information is packed before producing the music. For instance, a one-hour physical exercise would translate into a five-minute piece of music. In practice, the package could be implemented by averaging, for instance, whereby the heart beat interval data of a given time interval is represented by the mean heart rate of said time. The piece of music generated can be stored in mp3 format, for instance, whereby it can be stored on a computer hard disk and the file can be sent by e-mail.

The invention, i.e. the coding of heart rate information into a format that is presentable as sound collage, can be implemented in a clock mechanism of a heart rate monitor or on a separate computer. The coding can be implemented by means of an mp3 mixer or a midi-mixer or by means of software, for instance.

By means of the invention the data that is abundant and includes complex variations can be coded into a format that comprises the original information quality-wise and is also in a user-friendly form.

BRIEF DESCRIPTION OF THE DRAWINGS

In the following the invention will be described by means of preferred embodiments with reference to the attached figures, wherein.

DETAILED DESCRIPTION OF THE PREFERRED EMBODIMENTS

Figure 1:
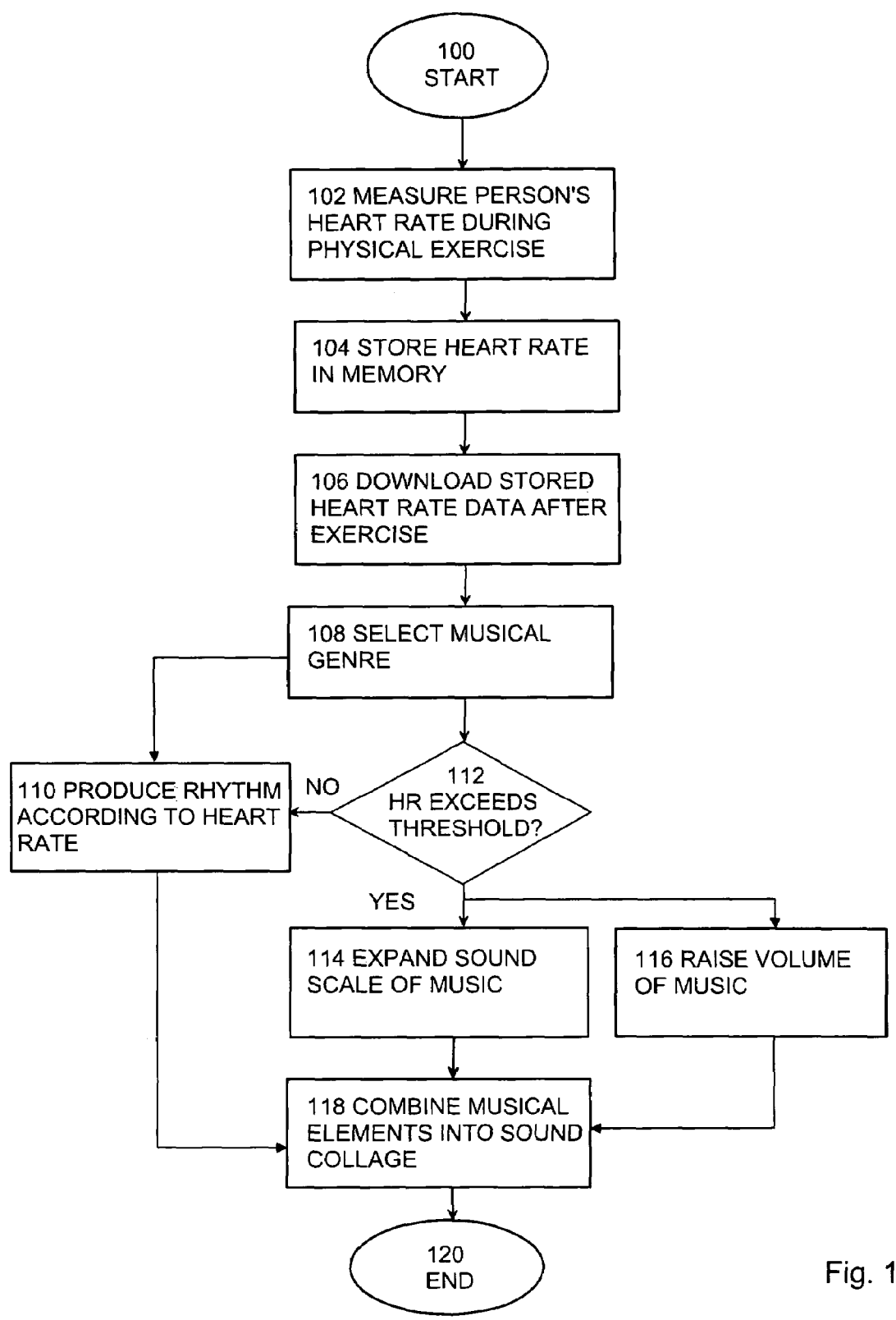
FIG. 1 shows one embodiment of the method.

FIG. 1 shows one preferred embodiment of the method according to the invention. A method step 102 represents heart rate measuring from a person in connection with a physical exercise or contest, for instance. The heart rate measurement may employ a heart rate monitor, which measures the heart rate from an electric signal generated by a heart beat, or alternatively, the heart rate is obtained by an optical measurement or a pressure measurement from a wrist, for instance. The measured heart beat interval information is stored during the measurement in a memory of the heart rate monitor, for instance, as described in step 104. In step 106, the stored heart beat interval information is downloaded after the physical exercise and the information can be analysed, for instance, by providing derived quantities, such as a heart rate mean, from the data. Steps 108 to 118 represent post-exercise operations, by which a sound collage is created from the measured heart rate information.

In step 108 there is selected a musical genre that will be used for producing the music. The genre may be e.g. jazz, pop, rock, classical music or the like. It is possible to select several musical genres, and consequently the genre can be changed, for instance, on the basis of variations in the heart rate. In that case, at a low heart rate it is possible to produce music using elements of classical music, but as the heart rate rises, it is possible to switch over to pop music. The musical elements used for music production can be elements in one or more keys, or they can be elements generated in a pentatonic scale. In step 110 there is selected the rhythm of the music on the basis of the changes in the heart rate. For instance, this refers to accelerating the beat, i.e. the tempo of the music as the heart rate rises.

In some embodiments it is possible to affect the content of the produced music also in other ways than by changing the rhythm of the music. The heart rate can be set a threshold value in accordance with condition 112, whereby the sound scale of the music is expanded in accordance with step 114 and/or the volume is raised in accordance with step 116. In step 118 the music, in which the rhythm and/or the sound scale and/or the volume have been modified on the basis of the heart rate, is combined into a sound collage. The created sound collage can be played on a heart rate monitor or any other device capable of sound reproduction. In one embodiment the music production also reacts to the heart rate change velocity, for instance, such that the rhythmical complexity of the music is increased as the heart rate derivative is positive, and correspondingly, it is decreased as the derivative is negative. The rhythmical complexity can be processed in the same way as the sound scale in step 110 or the volume in step 112, i.e. as the heart rate exceeds a given heart rate level, complexity is increased and below a given level there is less complexity. Or inversely, the sound scale and the volume can also be processed on the basis of changes in the derivative.

In connection with FIG. 1, the term 'heart rate' is used, which typically refers to the heart beat frequency per minute. In terms of measurement technique, the question is primarily about detecting a time difference between heartbeats, i.e. a heart beat interval. A heart rate per minute can be readily derived from the heart beat interval measurement.

Figure 2:
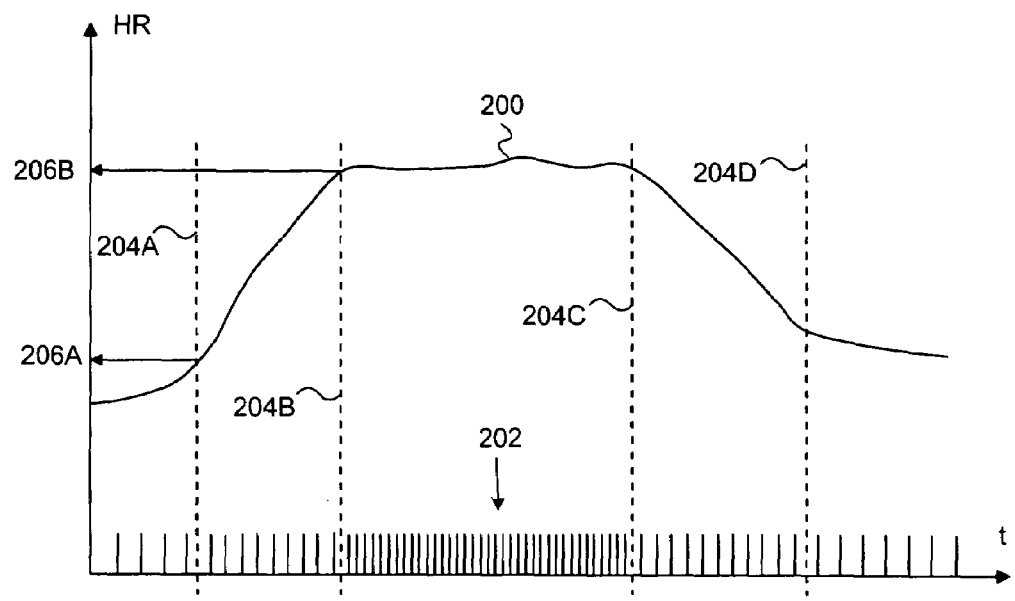
FIG. 2 illustrates how a rhythm of music is generated according to a heart rate.

FIG. 2 illustrates how the tempo of the music is generated on the basis of the heart beat interval information. In the figure a person's heart rate HR is represented on the y-axis as a function of time represented by the x-axis. Instead of the heart rate, it is possible to imagine that the y-axis represents the person's heart beat interval, whereby the heart beat interval becomes shorter in the upwardly direction of the y-axis. The person's heart rate 200 during a physical exercise is denoted with a continuous line, i.e. in the exercise concerned the heart rate starts rising from the time instant 204A onwards until it evens out at time instant 204B. Between 204B and 204C the heart rate practically remains on a constant level until it starts descending again at time instant 204C so as to even out again at time instant 204D. In FIG. 1 the time instant 204A involves exceeding a threshold value 206A when the tempo of the music accelerates. The rhythm indicated by vertical lines 202 doubles when the heart rate HR exceeds the threshold value 206A and further doubles when the heart rate exceeds the second threshold value 206B. In a corresponding manner the tempo of the music is slowed down as the heart rate is below given threshold values. It is obvious that the above-described doubling of the tempo is only given by way of example in the figure and the change of the tempo can be less than double or more than double.

Figure 3:
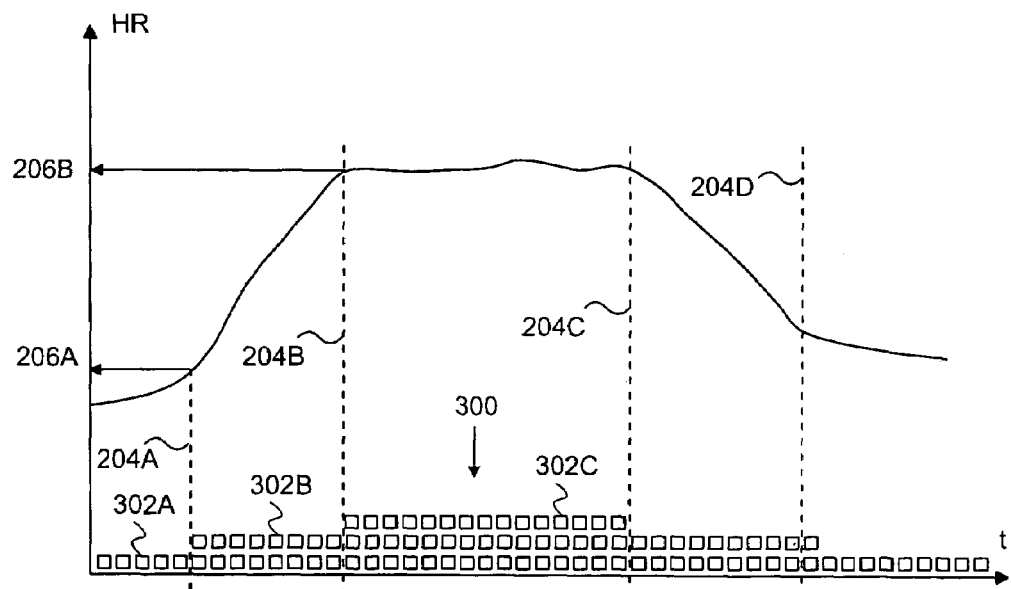
FIG. 3 illustrates how a sound scale is changed according to the heart rate.

FIG. 3 shows how the sound scale 300 is expanded on the basis of changes in the heart rate/heart beat intervals. At a heart rate level lower than the threshold value 206A the sound scale only comprises a limited amount of elements defining the sound scale. In a simplified manner, it is possible to illustrate the situation such that the sound scale 302A denotes classical music being played using one instrument only. At a level exceeding the threshold value 206A a second instrument comes along, which is illustrated by a sound expansion element 302B. Further, at a level exceeding the threshold value 206B the sound scale is expanded by a sound element 302C. The reduction of the sound scale 302A to 302C is performed inversely as the heart rate level comes down, i.e. finally as the heart rate falls the only remaining sound element is 302A.

Figure 4:
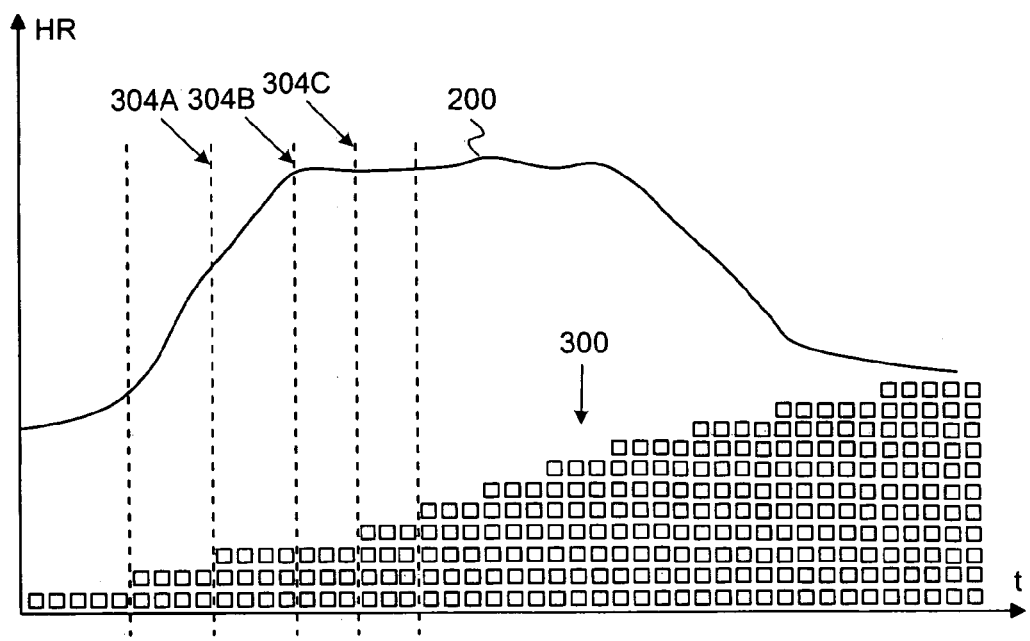
FIG. 4 illustrates how a sound scale is changed according to the heart rate.

FIG. 4 illustrates how the sound scale 300 is expanded according to the duration of a physical exercise. In other words, at the beginning of the exercise the sound scale is limited, but at the final stage of the exercise the scale can be expanded up to the maximum. The figure shows that sound elements can be added to the music at intervals that are the shorter the higher the heart rate level. For instance, the range from 304B to 304C represents an exercise performed at a higher heart rate level than the exercise period depicted by the range from 304A to 304B. So, for instance, the time interval 304A to 304B corresponds to a five-minute exercise, but the time interval 304B to 304C may correspond to a four-minute exercise, for instance. Hence, the sound scale can be expanded in a manner that is proportional to the exercise efficiency. On the basis of FIG. 4 it is also possible to consider changing the volume of the music in accordance with the heart rate. In one embodiment the volume is changed continuously, whereby the sound level is directly defined by the heart rate curve 200. The sound generation may also employ the same threshold value procedure as the one described in FIG. 2 for the tempo.

Figure 5:
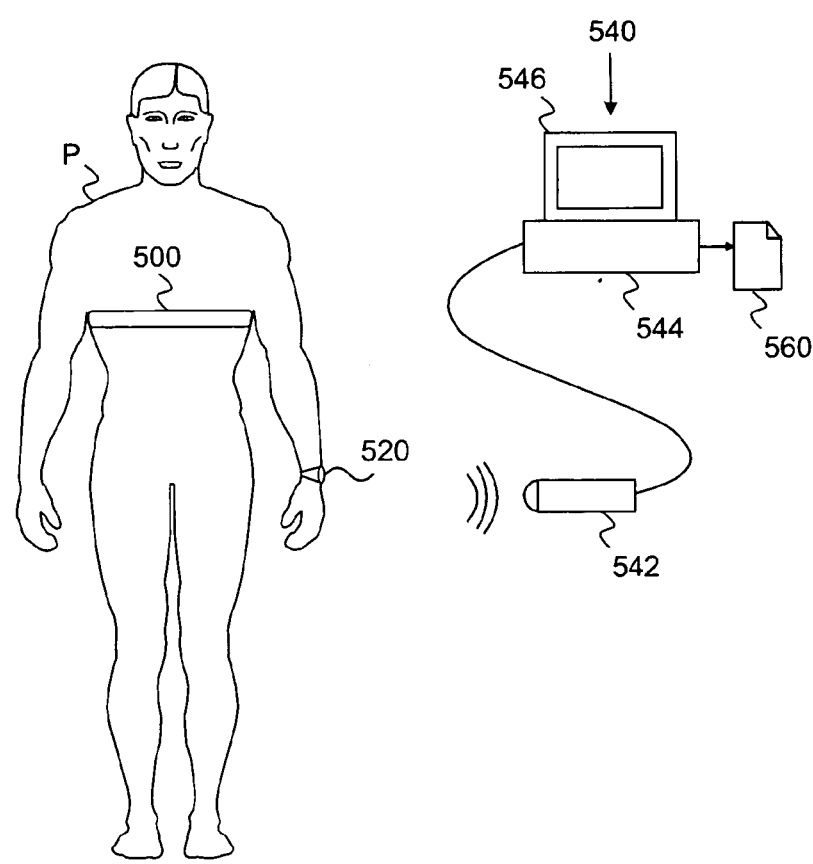
FIG. 5 shows one embodiment of a heart rate measuring arrangement.

Device solutions according to embodiments of the invention will be described by means of FIG. 5 and the subsequent figures. FIG. 5 shows a person P who wears a two-piece heart rate monitor during an exercise session. The heart rate monitor of FIG. 5 comprises a transmitter electrode belt 500 to be fitted around the chest and a wrist receiver 520 worn on the wrist. The transmitter electrode belt 500 measures the heart rate on the person's skin from an electric signal and transmits the measured information inductively, for instance, to the wrist receiver 520, which typically comprises a user interface of the heart rate monitor, such as function keys and a display. The receiver unit 520 is not necessarily a wrist-worn device unit but in cycling, for instance, the receiver unit can be attached to the handlebar of a bicycle. Even though FIG. 5 shows a two-piece heart rate monitor, the equipment used for measuring the heart beat intervals can also be a one-piece, wrist-worn device configuration, whereby the measuring from the pressure pulse and the presentation of the heart rate information all take place in the wrist-worn heart rate monitor, for instance.

In the solution of FIG. 5 the heart rate information is transferred to a computer 540 in the form of sound, for instance, using a microphone 546 connected to the computer 540. For instance, sound transfer refers here to converting bit information representing the heart rate data into sound such that a beep sound implemented by a piezo element of a clock corresponds to bit 1 and a silent period corresponds to bit 0. Prior to transfer, the information can be packed or the data can be transferred unpacked. The sound information is received by the microphone 542 of the computer 540. Data is processed by means of the central unit 544 and the display element 540 of the computer 540. The computer output is a sound collage 560 that can be reproduced on an audio system, such as a CD player or a computer. It should be noted that in FIG. 5 the computer is given as an embodiment only. Another alternative could be an embodiment with client/server approach utilizing the Internet, for instance. In that case the heart rate monitor or the computer, on which the measured heart rate information is stored, uses a server apparatus that is connected to the Internet and that returns a piece of music in response to the heart rate information transmitted thereto. The devices implementing the method of the invention can also be completely implemented in the heart rate monitor worn by the user, whereby no external computer for generating a sound file will be needed. This embodiment is illustrated by means of FIG. 6.

Figure 6:
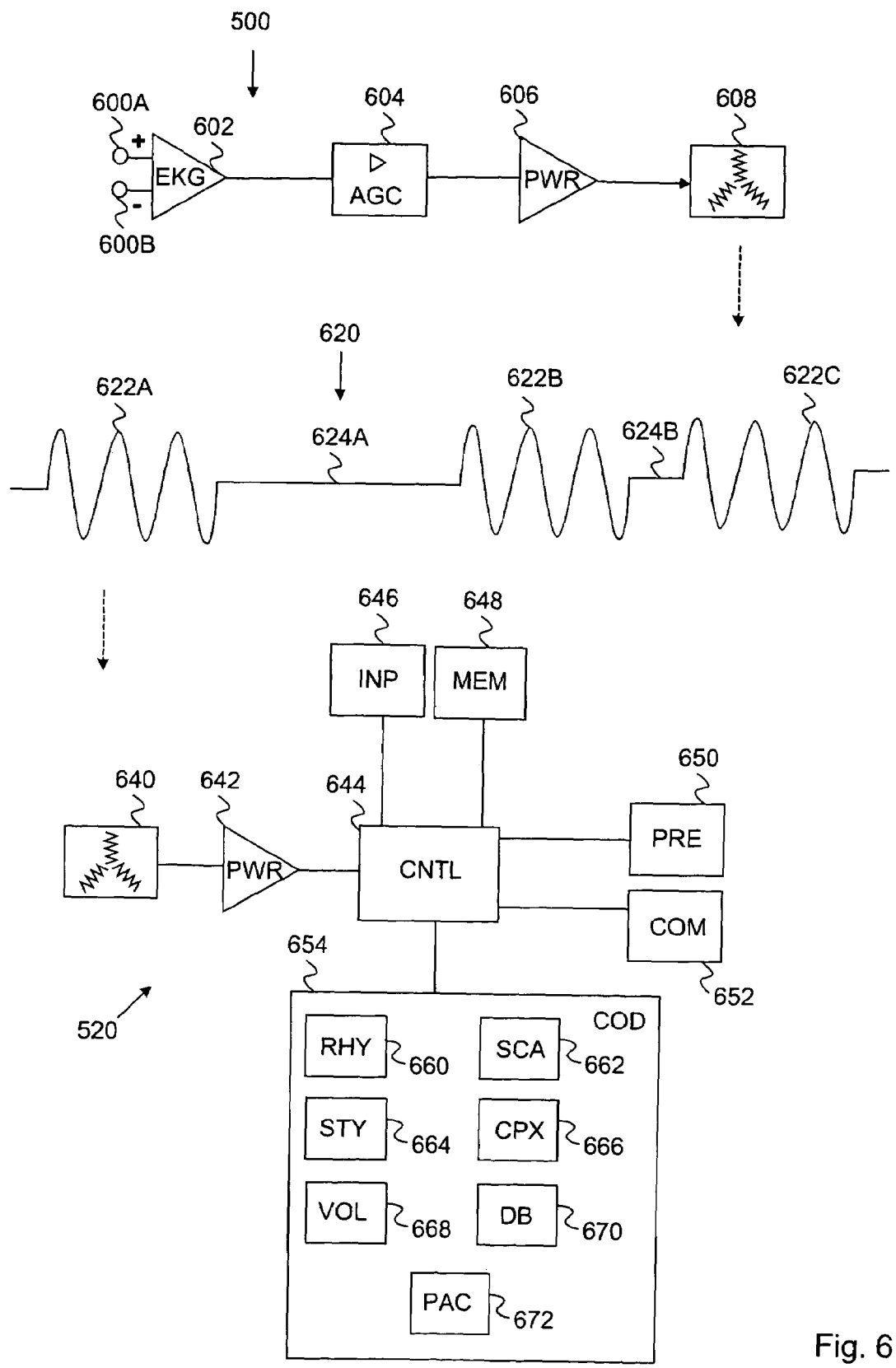
FIG. 6 shows a second embodiment of a device solution.

FIG. 6 shows one embodiment of an electrode belt 500 and a receiver 520 of the heart rate monitor. Device parts 600 to 608 of FIG. 6 represent the electrode belt and device parts 640 to 670 represent the receiver unit. Information between the electrode belt and the receiver unit is transmitted inductively, which is represented by a graph 620. For instance, one burst of 5 kHz 622A corresponds to one heart beat, or a cluster 622A to 622C of a plurality of bursts may correspond to one beat. The intervals 624A to 624B of the bursts 622A to 622C can be equal or different in length. The receiver unit 520 counts the heart rate on the basis of the measured heart beat intervals, whereby, in practice, the heart rate, i.e. the heart beat frequency is included in the transmission as coded in a period of time between the burst groups. Apart from the inductive transmission illustrated in FIG. 6, the information between the electrode belt and the receiver unit may alternatively be transmitted optically or through wires.

The electrode belt 500 measures the user's heart beat intervals with means 600A to 600B for measuring the heart rate. The measuring means are, for instance, electrodes that the heart rate monitor includes at least two but there may be even more. The electrodes 600A to 600B are connected to differential input poles of an ECG preamplifier 602, from which poles a signal is transmitted via an AGC amplifier 604 and a power amplifier 606 to a transmitter 608. In the case of inductive transmission the transmitter 608 is a transmitter coil that sends the heart rate information 620 to the receiver 520. The receiver unit 520 comprises a receiver coil 640, from which the received signal is applied via an amplifier 642 to control means 644 that are implemented by means of software on a microprocessor of the receiver unit. The function of the control means is to control and coordinate the various parts and functions of the heart rate monitor.

The receiver unit comprises entering means 646 for entering user parameters and operational settings and commands into the heart rate monitor. The entering means 646 can be implemented as press keys in a watch-like receiver unit. The entering means may also denote a microphone, whereby the entering interface serves as a speech/sound interface towards the user or an external computer. The entering means may also be a data communications port for data input from external equipment. The receiver 520 also comprises means 648 for storing heart rate information during the user's exercise session. In this connection the heart rate information to be stored can be, for instance, heart rate as a function of time, quantities derived from the heart rate, such as mean values of the heart rate, data on variations in the heart rate or the like. The receiver may also comprise means 650 for presenting information. Information to be presented by the presenting means 650 may include, for instance, the heart rate during the exercise and/or a quantity derived from the heart rate, such as a mean value. The presenting means 650 can also be employed for showing the user selection information relating to the selection of heart rate monitor settings or other use-related information, such as information on ongoing data transmission to an external computer. Thus, the presenting means can be a display device, such as a liquid crystal display, for instance. The presenting means can also be audio equipment, and thus the presenting means can reproduce audio-type information, such as music, i.e. the music produced by the method of the invention can be reproduced on the wrist-worn device of the heart rate monitor of FIG. 6. Further, the presenting means allow visual illustration of how the exercise proceeds, while the produced music is played for the user.

In one embodiment the heart rate monitor also comprises communicating means 652, with which the data measured and/or generated in the heart rate monitor can be transferred to external equipment, such as a computer or a mobile telephone. The transferred data can be measured heart rate data that is downloaded from the memory 648 of the receiver unit 520. The transferred data can also be heart beat interval information that is packed or otherwise processed in the receiver unit. The communicating unit can be implemented in a variety of ways, equipment required for implementation of radio, sound or optical connections given as examples. In the alternative where sound is implemented, the sound is generated by means of a piezo element.

The heart rate monitor further comprises means 654 for coding the heart beat interval information into musical format. The coding means 654 comprise means 660 for providing the music with tempo on the basis of the measured heart beat intervals. Further, in one embodiment the coding means 654 comprise means 664 for selecting a musical genre. In practice, the selecting means 664 may act in cooperation with the function keys and the display of the heart rate monitor such that the display shows a menu of various musical genres, from which the user may select the desired genre with the function keys. It is possible to select several genres for a particular physical exercise and the use thereof can be controlled in coding by means of threshold values. Thus, for instance, classical music can be used in a low heart rate zone, whereas heavy rock music is used in a high heart rate zone. Further, the coding means 654 may comprise means 662 for changing a sound scale. The means 662 for changing the sound scale may operate, for instance, such that a limited sound scale is used in a low heart rate zone, but in a higher heart rate zone the sound scale is expanded. The sound scale can also be controlled by means of a heart rate derivative, for instance, such that as the heart rate derivative is strongly positive a wide sound scale is used and as the derivative turns negative the sound scale is reduced. In one embodiment the coding means 654 comprise means 666 for changing the complexity of the music, i.e. rhythmical variations. The complexity can be adjusted on the basis of the heart rate derivative and the length of the heart beat intervals, for instance. Thus, as the heart beat interval becomes shorter or the derivative is positive it is possible to increase the complexity of the music, for instance. In one embodiment the heart rate monitor comprises means 668 for controlling the volume. For instance, the volume can be controlled in accordance with the heart rate, and thus the volume is raised as the heart rate rises and reduced as the heart rate falls.

In the heart rate monitor music can be produced digitally with means 670 for combining sound elements. In this connection a sound element refers to short digital data sequences that can be combined by means of certain rules. It is assumed that at a given time instant the sound scale used is one, i.e. one instrument is in use, for instance. At each time instant the combining means browse through such sound elements that could be combined to the sound element added at the previous time instant. The selection of a subsequent sound element can utilize the desired rules or the element can be selected randomly from among the available sound elements. When two or more sound elements are used at a given time instant for sound production, it will be necessary to assess the feasibility of sound element summing combination performed at each time instant.

In one embodiment the heart rate monitor comprises means 672 for packing heart beat interval information. The packing can be performed by averaging the heart beat interval information, for instance. In packing the heart beat interval information is compressed such that the packed data is shorter in duration than the actual measuring time. The packing ratio can be tenfold or hundredfold, for instance.

Even though FIG. 6 describes music production in a heart rate monitor carried on a person, the functionality for coding music can also be implemented on an external computer, for instance. Further, even though FIG. 6 shows a two-piece heart rate monitor, the functionality can also be implemented in a one-piece heart rate monitor worn on the wrist or the chest.

The invention can be implemented by means of software, separate logic components, as an ASIC or in any other known manner.

Thus, the method for coding heart rate information in accordance with the present invention includes measuring a person's heart beat intervals during a physical exercise, storing the measured heart beat interval information, packing the measured heart beat interval information, and coding the packed heart beat interval information into a format that is presentable after the exercise as a sound collage such that the rhythm of the sound collage depends on the measured heart beat intervals and the duration of the sound collage is shorter than the time spent for measuring the heart beat intervals.

The arrangement for coding heart rate information in accordance with the present invention includes means for measuring a person's heart beat intervals, means for storing the measured heart beat interval information, means for packing the measured heart beat interval information, and means for coding the packed heart beat interval information stored in the storing means into a sound collage that is shorter in duration than the measurement time. The coding means includes means for selecting the rhythm for the music in the sound collage on the basis of the measured heart beat intervals.

It is apparent to a person skilled in the art that as technology advances the basic idea of the invention can be implemented in a variety of ways. The invention and the embodiments thereof are thus not restricted to the above-described examples but they may vary within the scope of the claims.

The invention claimed is:

1. A method for coding heart rate information, the method comprising:
measuring a person's heart beat intervals during a physical exercise;
storing the measured heart beat interval information;
packing the measured heart beat interval information;
coding at least a portion of the packed heart beat interval information into a format that is presentable after the exercise as a sound collage such that the rhythm of the sound collage depends on the measured heart beat intervals, the duration of the sound collage being shorter than the time spent for measuring the heart beat intervals.

2. The method of claim 1, wherein the step of coding comprises:
selecting a musical genre of the sound collage to be used in coding.

3. The method of claim 1, wherein the music of the sound collage to be coded consists of digital sound packets that can be added to one another in temporal sequence and/or combined by summing at a given time instant.

4. The method of claim 1, wherein the step of coding comprises:
changing the sound scale of the music in the sound collage on the basis of changes in the length of the heart beat intervals.

5. The method of claim 1, wherein the step of coding comprises:
augmenting the sound scale of the music in the sound collage in accordance with the duration of the heart beat interval measurement.

6. The method of claim 1, wherein the step of coding comprises: changing the rhythmical complexity of the music in the sound collage on the basis of the variation rate of the heart beat intervals.

7. The method of claim 1, wherein the step of coding comprises: changing the volume of the music in the sound collage on the basis of the measured lengths of the heart beat intervals.

8. The method of claim 1, wherein the coding is performed after the physical exercise on the whole heart beat interval data collected from the physical exercise.

9. The method of claim 1, wherein the step of coding comprises: generating from the sound collage music a sound collage that can be stored in a storing means.

10. An arrangement for coding heart rate information, comprising:
means for measuring a person's heart beat intervals;
means for storing the measured heart beat interval information;
means for packing the measured heart beat interval information;
means for coding at least a portion of the packed heart beat interval information stored in the storing means into a sound collage, the sound collage being shorter in duration than the time spent measuring the heart beat intervals, the coding means comprising means for selecting the rhythm for music in the sound collage on the basis of the measured heart beat intervals, the coding means comprising means for selecting a musical genre of the sound collage to be used in the coding.

11. The arrangement of claim 10, wherein the arrangement is a heart rate monitor.

12. The arrangement of claim 11 wherein the heart rate monitor comprises means for presenting the generated sound collage.

13. The arrangement of claim 12, wherein the presenting means are a piezo element of the heart rate monitor.

14. The arrangement of claim 10, wherein the coding means comprise means for joining together digital sound packets that can be added to one another in temporal sequence and/or combined by summing at a given time instant.

15. An arrangement for coding heart rate information, comprising:
means for measuring a person's heart beat intervals;
means for storing the measured heart beat interval information;
means for packing the measured heart beat interval information;
means for coding at least a portion of the packed heart beat interval information stored in the storing means into a sound collage, the sound collage being shorter in duration than the time spent measuring the heart beat intervals, the coding means comprising means for selecting rhythm for the music in the sound collage on the basis of the measured heart beat intervals, the coding means comprising means for changing the rhythmical complexity of the music in the sound collage on the basis of the variation rate of the heart beat intervals.

16. An arrangement for coding heart rate information, comprising:
means for measuring a person's heart beat intervals;
means for storing the measured heart beat interval information;
means for packing the measured heart beat interval information;
means for coding at least a portion of the packed heart beat interval information stored in the storing means into a sound collage, the sound collage being shorter in duration than the time spent measuring the heart beat intervals, the coding means comprising means for selecting rhythm for the music in the sound collage on the basis of the measured heart beat intervals, the coding means comprising means for changing the volume of the music in the sound collage on the basis of the measured the heart beat intervals.

17. The arrangement of claim 14, wherein the measurement of the heart rate information takes place during a physically strenuous exercise.

18. The arrangement of claim 14, wherein the arrangement comprises means for storing the sound collage in a storing means.

19. An arrangement for coding heart rate information, comprising:
means for measuring a person's heart beat intervals;
means for storing the measured heart beat interval information;
means for packing the measured heart beat interval information;
means for coding at least a portion of the packed heart beat interval informaion stored in the storing means into a sound collage, the sound collage being shorter in duration than the time spent measuring the heart beat intervals, the coding means comprising means for selecting rhythm for the music in the sound collage on the basis of the measured heart beat intervals, the coding means comprising means for changing the sound scale of the music in the sound collage on the basis of changes in the length of the heart beat intervals.

20. An arrangement for coding heart rate information, comprising:
means for measuring a person's heart beat intervals;
means for storing the measured heart beat interval information;
means for packing the measured heart beat interval information;
means for coding at least a portion of the packed heart beat interval information stored in the storing means into a sound collage, the sound collage being shorter in duration than the time spent measuring the heart beat intervals, the coding means comprising means for selecting rhythm for the music in the sound collage on the basis of the measured heart beat intervals, the coding means comprising means for changing the sound scale of the music in the sound collage in accordance with the duration of the heart beat interval measurement.

* * * * *